US00PP35798P3

(12) United States Plant Patent
Yuki et al.

(10) Patent No.: US PP35,798 P3
(45) Date of Patent: May 7, 2024

(54) ***PHALAENOPSIS* PLANT NAMED '311NR'**

(50) Latin Name: *Phalaenopsis hybrida*
Varietal Denomination: 311NR

(71) Applicant: ISHIHARA SANGYO KAISHA, LTD., Osaka (JP)

(72) Inventors: Shunji Yuki, Shiga (JP); Masahiro Mii, Tokyo (JP); Dong Poh Chin, Tokyo (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 17/683,638

(22) Filed: Mar. 1, 2022

(65) Prior Publication Data

US 2023/0037288 P1 Feb. 2, 2023

(30) Foreign Application Priority Data

Aug. 2, 2021 (JP) ..... 35624

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

(56) References Cited

U.S. PATENT DOCUMENTS

PP34,055 P2 * 3/2022 Van Swieten ..... A01H 6/62
Plt./311

FOREIGN PATENT DOCUMENTS

WO WO-2008111650 A1 * 9/2008 ..... C12N 15/825

OTHER PUBLICATIONS https://www.greenhousegrower.com/production/plant-culture/genetic-modification-produces-true-blue-orchid/; Jan. 27, 2014; 2 pages.*
https://www.orchids.org/grexes/phalaenopsis-wedding-promenade; Aug. 4, 2023; 7 pages.*
Ishiharasangyo Kaisha, Ltd., Biological diversity risk assessment dossier for bluish purple phalanopsis, (CcF3'5'H, Phalaenopsis Wedding Promenade) (311NR). 115 pages. Oct. 30, 2020.

* cited by examiner

*Primary Examiner* — Kent L Bell
(74) *Attorney, Agent, or Firm* — McCarter & English, LLP; David G. Conlin; Dylan M. Blumenthal

(57) ABSTRACT

'311NR' is a new and distinct variety of *Phalaenopsis* orchid; the instant variety is distinguishable from other cultivars known to the Inventors by its dark purple flower petals, overall plant length, and width of flower and flower petals.

10 Drawing Sheets

Latin name of the genus and species of the plant claimed: *Phalaenopsis hybrida.*

Varietal denomination: '311NR'.

RELATED APPLICATIONS

This application claims priority to Japanese Plant Variety Protection Application No.: 35624, filed Aug. 2, 2021, pursuant to 35 U.S.C. § 119(f).

BACKGROUND OF THE NEW PLANT

The present invention comprises a new *Phalaenopsis*, botanically known as *Phalaenopsis hybrida* and hereafter referred to by the new variety name '311NR'.

The candidate variety '311NR' was produced, in part, by genetic recombination. Anthocyanins, one of the pigments that determine flower color, are flavonoid glycosides, and their aglycone (anthocyanidins) structures allow them to produce a wide range of colors. For example, if the anthocyanidin is cyanidin, it produces a red-purple color, and if the anthocyanidin is delphinidin, it produces a blue-purple color. Therefore, the type and amount of anthocyanidins in the petals is an important factor for determining flower color. Only the cyanidin-type anthocyanin has been detected in *Phalaenopsis* varieties with red-purple flowers, such as 'Wedding Promenade'. The candidate variety was produced by introducing, to *Phalaenopsis* 'Wedding Promenade' (not patented), F3' 5' H gene derived from *Commelina communis*. Expression of F3'5'H in petals of *Phalaenopsis* converts part of the cyanidin to delphinidin, resulting in a change in flower color to a blue-purple color.

To asexually reproduce '311NR', axillary buds of flower stalks were cultured in a culture medium containing plant hormones (0.1 mg/l NAA, 1 mg/l BA) so that protocorm-like bodies (PLB) were induced and grown. Thereafter, PLB were redifferentiated in a hormone-free culture medium and flask seedlings were prepared.

'311NR' originates from a controlled breeding program in Kusatsu, Shiga, Japan.

BRIEF SUMMARY OF THE INVENTION

'311NR' has not been observed under all possible environmental conditions. The phenotype may vary significantly with variations in environment such as temperature, light intensity, and day length.

Plant Breeder's Rights for this cultivar have been applied for in Japan on Aug. 2, 2021. '311NR' has not been made publicly available more than one year prior to the filing of this application.

The following traits have been repeatedly observed and are determined to be basic characteristics of the new variety. The combination of these characteristics distinguishes this *Phalaenopsis* as a new and distinct variety.

BRIEF DESCRIPTION OF THE PHOTOGRAPHS

The accompanying photographic drawings show typical foliate characteristics of '311NR' with colors being as true as possible with an illustration of this type.

DETAILED BOTANICAL DESCRIPTION

TABLE 1

DIFFERENCES BETWEEN THE NEW VARIETY AND SIMILAR VARIETIES

Figure 1:
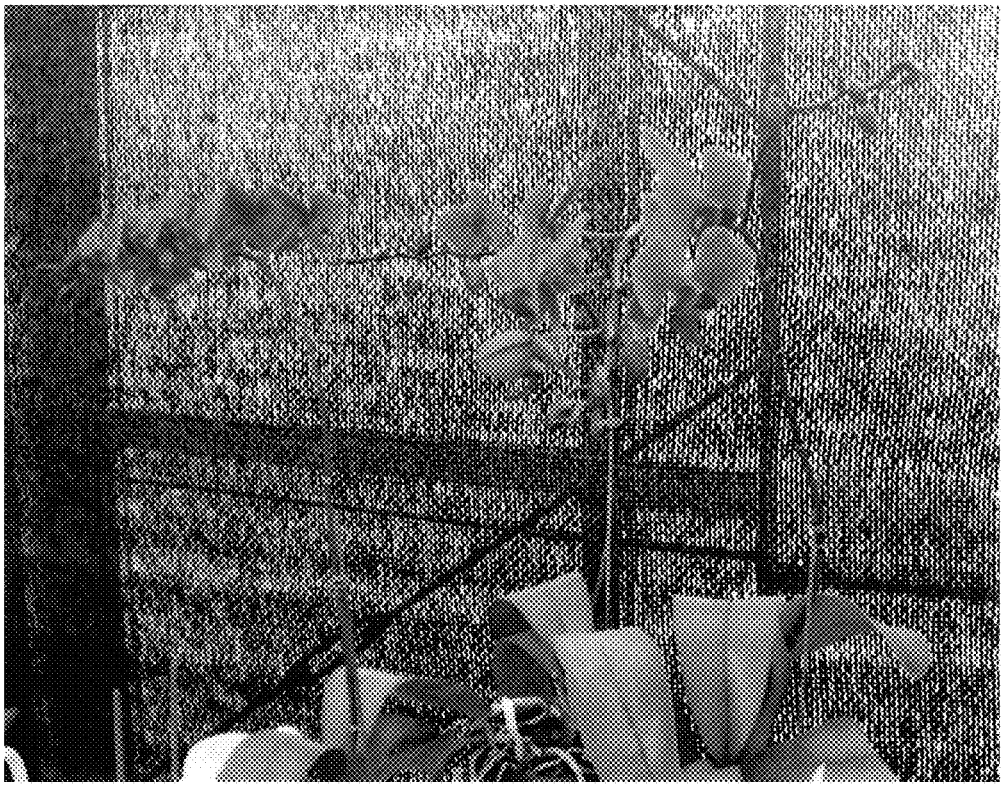
FIG. 1 shows photographic drawings of cultivation of '311NR' in the greenhouse location four years after planting.
Figure 2:
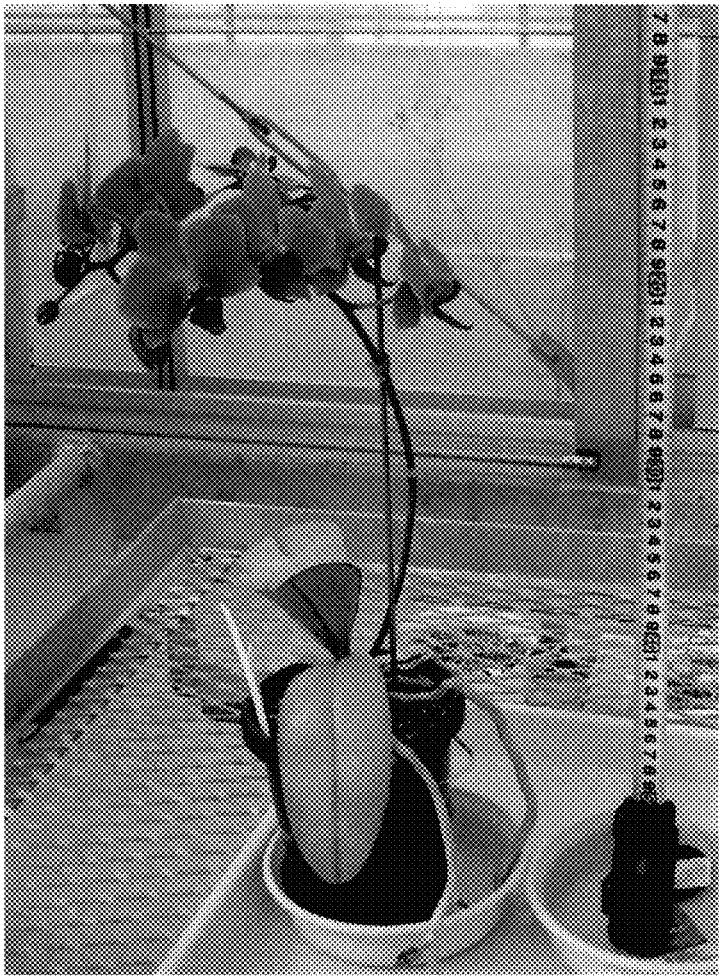
FIG. 2 shows an entire view of the plant two years after planting.
Figure 3:
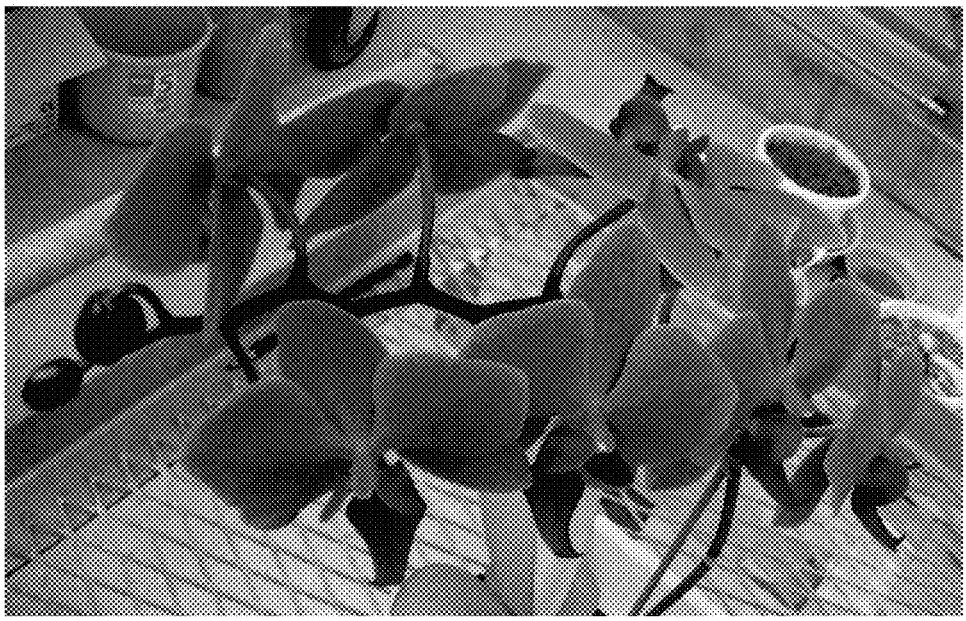
FIG. 3 shows inflorescence of the plant two years after planting.
Figure 4:
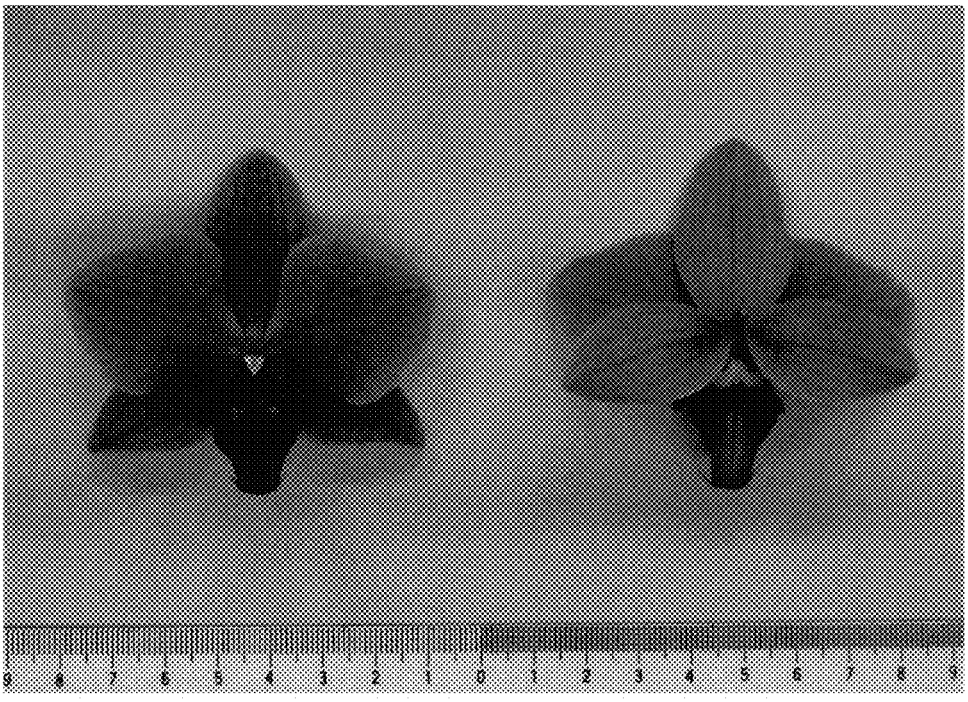
FIG. 4 shows an enlarged depiction of flowers from an aerial point of view two years after planting.
Figure 5:
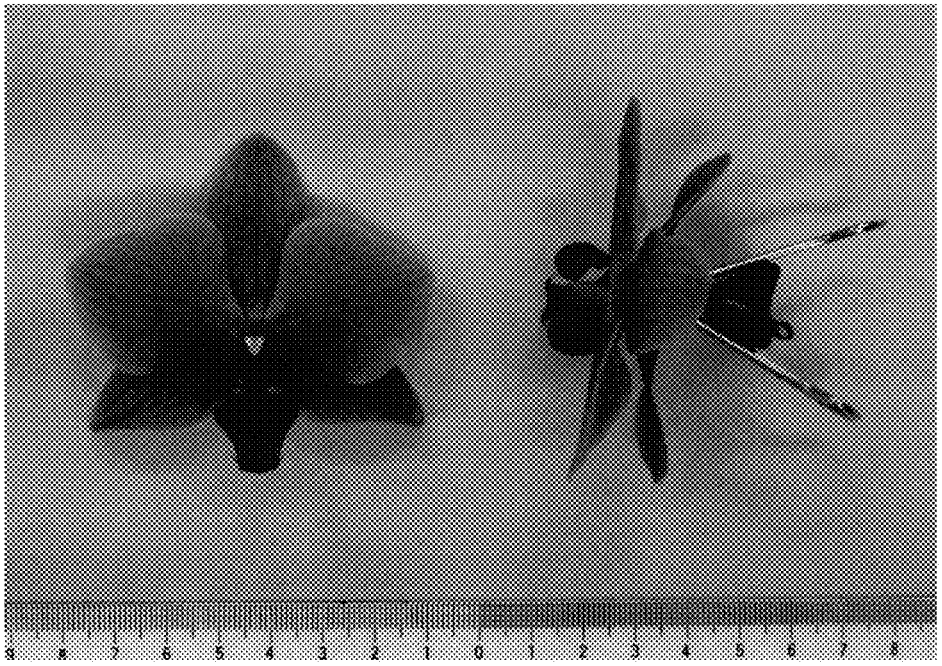
FIG. 5 shows an enlarged depiction of flowers from aerial and side points of view two years after planting.
Figure 6:
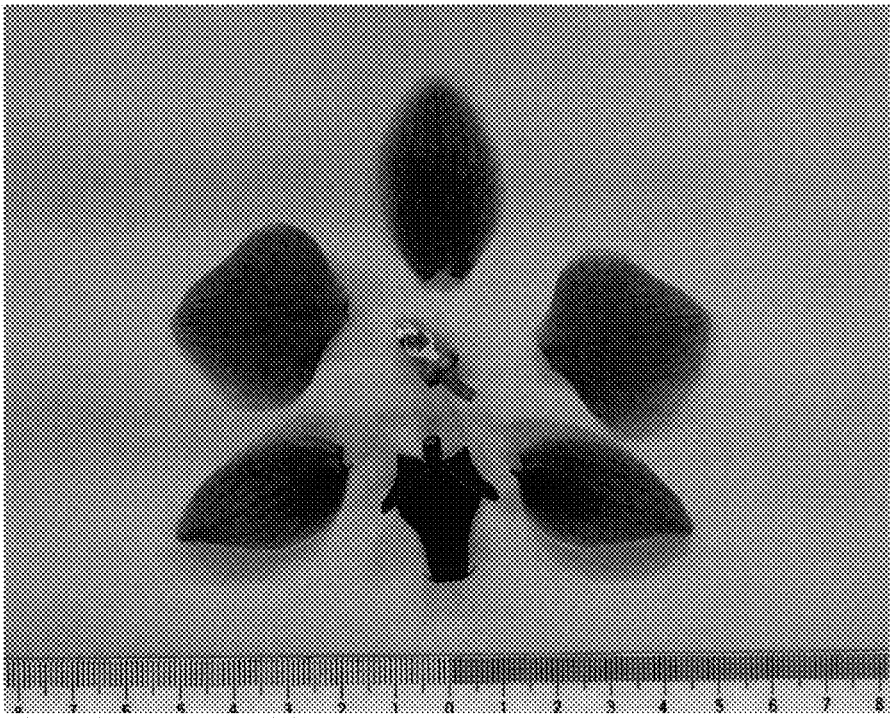
FIG. 6 shows an exploded depiction of a flower from an aerial view two years after planting.
Figure 7:
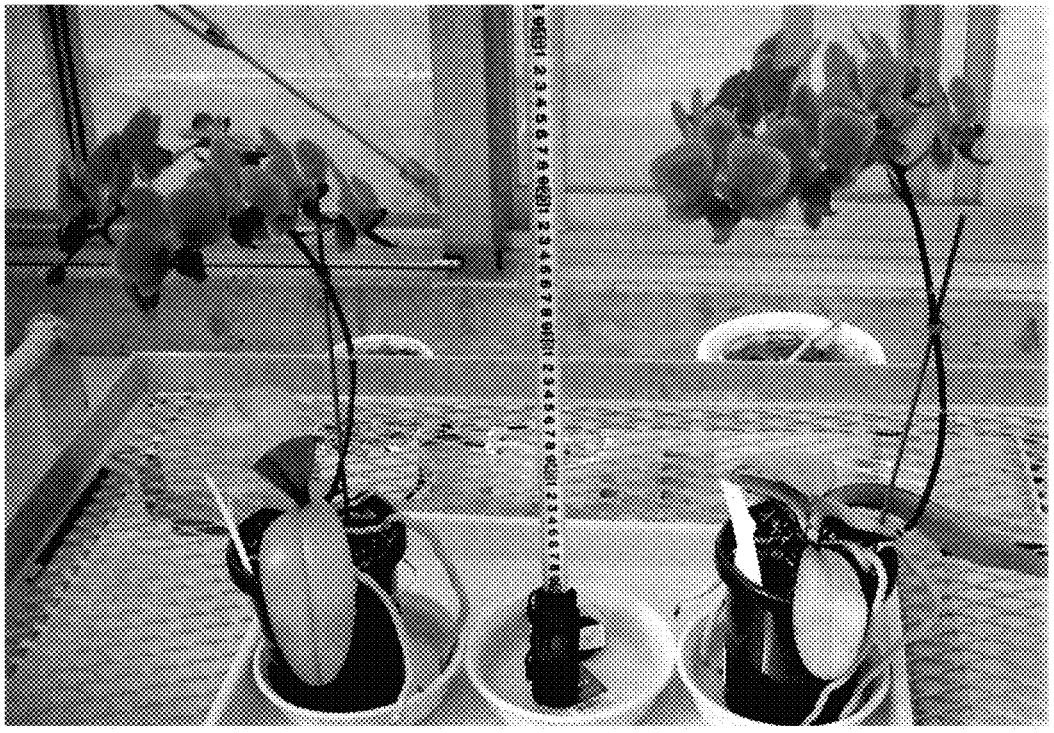
FIG. 7 shows a comparative depiction of entire plants '311NR' (left) and parent variety 'Wedding Promenade' (right) two years after planting.
Figure 8:
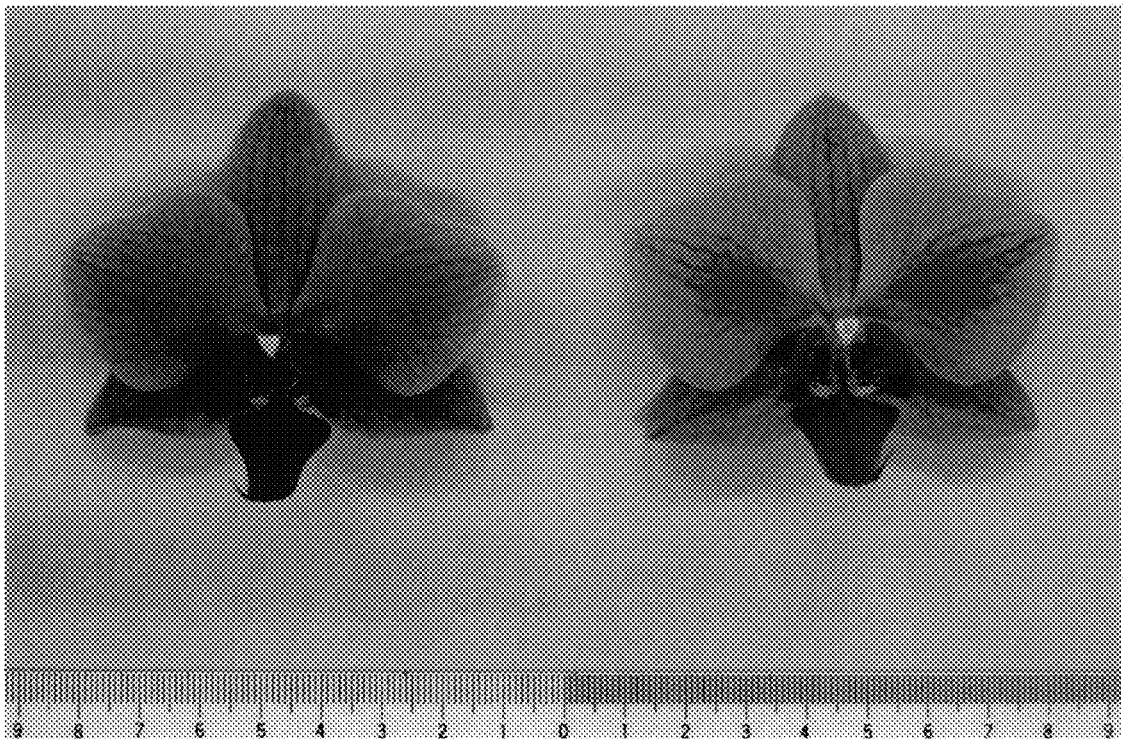
FIG. 8 shows a comparative depiction of flowers from '311NR' (left) and parent variety 'Wedding Promenade' (right) from an aerial point of view two years after planting.
Figure 9:
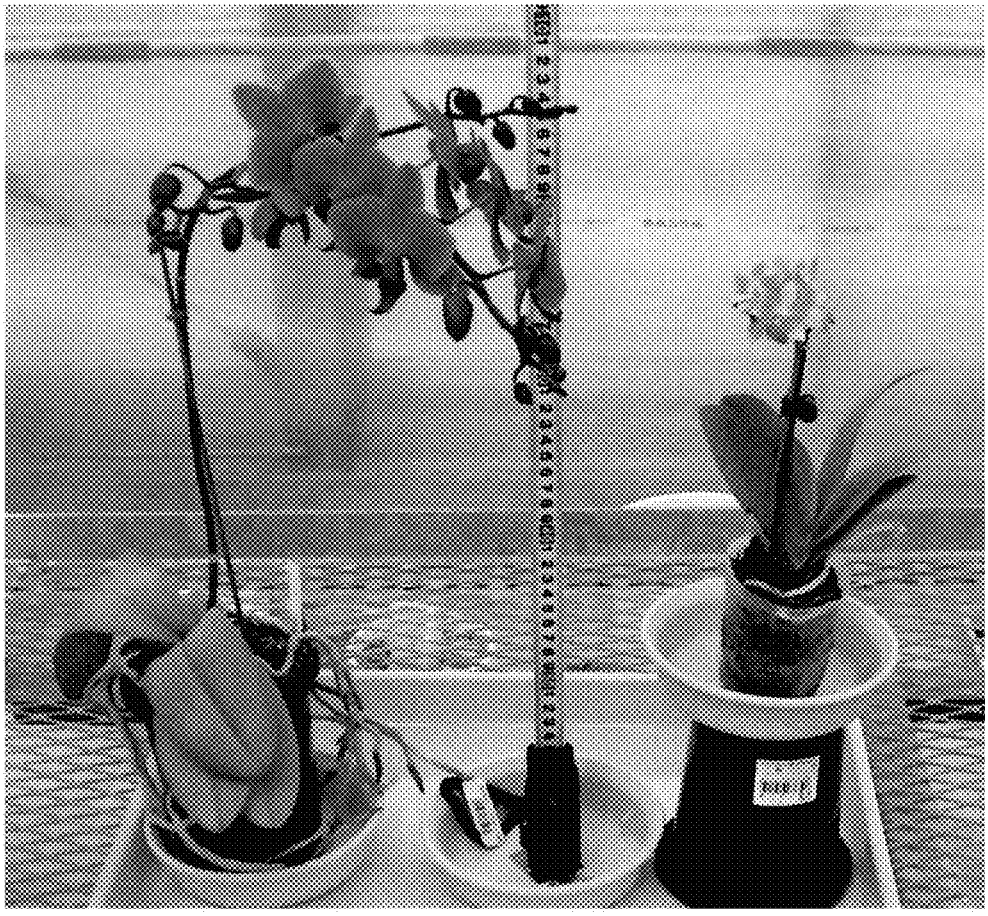
FIG. 9 shows a comparative depiction of entire plants '311NR' (left) and 'Summer Rose' (right) (not patented) approximately two years after planting.
Figure 10:
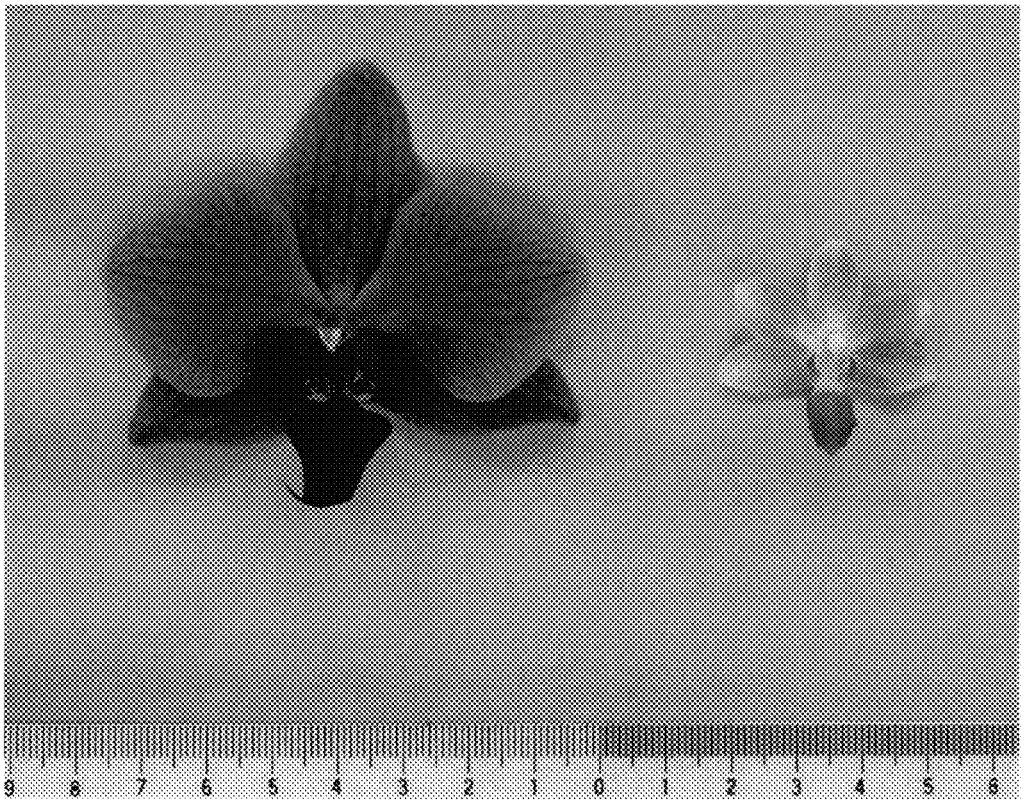
FIG. 10 shows a comparative depiction of flowers from '311NR' (left) and 'Summer Rose' (right) from an aerial point of view approximately two years after planting.

| Name of Similar Variety | Description of Characteristics | Characteristics of Similar Variety | Characteristics of '311NR' |
|---|---|---|---|
| 'Wedding Promenade' | Petal: ground color of upper side | N74D, N78D | 91A |
| 'Wedding Promenade' | Petal: over color (if present) | N74B, N78B | N88A, N89A |
| 'Wedding Promenade' | Petal: color of spots | 75D | 91B |
| 'Wedding Promenade' | Petal: color of stripes | N74A, N78A | N89B |
| 'Wedding Promenade' | Petal: color of netting | N74A, N78A | N89B |
| 'Summer Rose' | Plant: length | 26 cm | 51 cm |
| 'Summer Rose' | Flower: width in front view | 38 mm | 70 mm |
| 'Summer Rose' | Petal: ground color of upper side | NN155C | 91A |
| 'Summer Rose' | Petal: over color (if present) | N87B, N87C | N88A, N89A |
| 'Summer Rose' | Petal: color of stripes | N87B, N87C | N89B |

Color chart used: Royal Horticultural Society Colour Chart (R.H.S.) $5^{th}$ edition.

The following description is applied to our plants that are 24 months old as of the time of the measurements.

Plant:

*Length*.—51 cm.
*Width*.—29 cm.
*Height*.—14 cm.
*Vigor*.—Medium.

Leaf:

*Variegation*.—Absent.
*Spots on upper side*.—Absent.
*Typical number*.—6.
*Length*.—20 cm.
*Width*.—8 cm.
*Thickness*.—1.6 mm.
*Position of broadest part*.—Middle.
*Shape*.—Oblong to narrowly obovate.
*Apex*.—Obtuse.
*Margin*.—Entire.
*Base*.—Acute.
*Blade angle with petiole*.—Horizontal.
*Texture* (*both surfaces*).—Smooth, glabrous.
*Color of upper surface*.—138A.
*Color of lower surface*.—138A.
*Venation pattern*.—Parallel.
*Venation color* (*upper*).—N137B.
*Venation color* (*lower*).—N186B.

Peduncle:

*Growth habit*.—Upright.
*Number*.—About 1 to 2.
*Length*.—35 cm.
*Diameter*.—5 mm.
*Strength*.—Strong.
*Aspect*.—Upright to outwardly arching.
*Texture*.—Smooth, glabrous.
*Internode length*.—6 cm.
*Color*.—147A.

Pedicel:

*Number*.—About 10 to 15.
*Length*.—28 mm.
*Diameter*.—2.5 mm.
*Strength*.—Moderately strong.
*Aspect*.—Horizontal.
*Texture*.—Smooth, glabrous.
*Color*.—91A.

Inflorescence:

*Appearance*.—Zygomorphic flowers arranged with axillary branched racemes.
*Number*.—About 1 to 2.
*Height*.—36 cm.
*Length*.—20 cm.

*Width.*—12 cm.
*Lastingness.*—2 to 3 months.
Flower:
*Width in front view.*—70 mm.
*Height.*—61 mm.
*Shape.*—With three petals, two lateral petals and one center petal transformed into a labellum and three sepals.
*Lastingness.*—About 4 to 6 weeks.
*Fragrance.*—None detected.
*Bud length.*—19 mm.
*Bud width.*—14 mm.
*Bud shape.*—Ovate.
*Bud color:.*—N92A.
Dorsal sepal:
*Shape.*—Elliptic.
*Length.*—3.8 cm.
*Width.*—2.2 cm.
*Apex.*—Acute.
*Margin.*—Entire.
*Base descriptor.*—Ovate.
*Position of the broadest part.*—Middle.
*Texture (both surfaces).*—Smooth, glabrous.
*Color (both faces).*—N89C.
Lateral sepal:
*Number.*—2.
*Shape.*—Elliptic.
*Length.*—3.2 cm.
*Width.*—2.1 cm.
*Apex.*—Acute.
*Margin.*—Entire and weakly undulate.
*Base descriptor.*—Ovate.
*Position of the broadest part.*—Middle.
*Texture (both faces).*—Smooth, glabrous.
*Color (both faces).*—N89C.
Labellum:
*Shape.*—Three-parted with two lateral lobes and an apical lobe.
*Length.*—2.4 cm.
*Width.*—2.2 cm.
*Whiskers.*—Present.
*Number of whiskers.*—2.
*Color.*—N89A.
Lateral lobe:
*Number.*—2.
*Shape.*—Ovate.
*Length.*—1.3 cm.
*Width.*—1.2 cm.
*Apex.*—Obtuse.
*Margin.*—Entire.
*Texture (both faces).*—Smooth, glabrous.
*Color (both faces).*—N89A.
Apical lobe:
*Shape.*—Obtrullate.
*Length.*—2.0 cm.
*Width.*—1.6 cm.
*Apex.*—Terminated with 2 whiskers.
*Margin.*—Entire.
*Texture (both faces).*—Smooth, glabrous.
*Color (upper face).*—N89A.
*Color (lower face).*—N89B.
Callus:
*Height.*—4 mm.
*Length.*—4 mm.
*Width.*—3.5 mm.
*Color.*—13C.
Column:
*Length.*—7.5 mm.
*Diameter.*—4 mm.
*Color.*—N89B.
Pollinia:
*Number.*—2.
*Diameter.*—1 mm.
*Color.*—N25B.
Ovary:
*Length.*—6.5 mm.
*Diameter.*—2 mm.
*Color.*—N89C.
Petal:
*Lateral petal arrangement.*—Two lateral petals are separate.
*Lateral petal number.*—2.
*Shape.*—Rounded rhombus.
*Apex.*—Ovate.
*Margin.*—Entire and weakly undulate.
*Base descriptor.*—Acute.
*Length.*—3.5 cm.
*Width.*—3.2 cm.
*Position of the broadest part.*—Middle.
*Ground color of upper side.*—91A.
*Over color of upper side.*—N88A, N89A.
*Number of spots of upper side.*—25.
*Color of spots of upper side.*—91B.
*Number of stripes of upper side.*—8.
*Color of stripes of upper side.*—N89B.
*Density of netting of upper side.*—Low.
*Color of netting of upper side.*—N89B.
*Ground color of lower side.*—91A.
*Over color of lower side.*—92A.
*Spots of lower side.*—Absent.
*Color of stripes of lower side.*—N89C.
*Color of netting of lower side.*—N89C.
Root:
*Color of root.*—NN155B.
*Color of lateral root.*—NN155B.
*Color of aerial root.*—192B.

OTHER CHARACTERISTICS

Commercial classification: Ornament, pot flower, or cut flower.

Method of preservation and storage: Cultured in pod in greenhouse.

Time for seeding and planting: Early January to later December.

Growing stage, including flowering: Middle February to late May.

Young seedlings of '311NR' in flasks are transplanted into pots. The potted plants are grown at high temperatures, in the range of 28 to 32 degrees Celsius, into mature plants of flowering size in 18 months. The mature potted plants are then cultivated at low temperatures, in the range of 18 to 23 degrees Celsius, for 6 months to finish flowering.

What is claimed is:

1. A new and distinct variety of *Phalaenopsis* plant named '311NR', substantially as illustrated and described herein.

* * * * *